(12) United States Patent
Stefanov et al.

(10) Patent No.: US 8,293,949 B2
(45) Date of Patent: Oct. 23, 2012

(54) PROCESS FOR PRODUCING LOW COLOR GLYCOLS

(75) Inventors: Zdravko I. Stefanov, Lake Jackson, TX (US); Jean Paul Chauvel, Jr., Lake Jackson, TX (US); Abraham Gonzalez, Baton Rouge, LA (US); Istvan Lengyel, Lake Jackson, TX (US)

(73) Assignee: Dow Technology Investments LLC, Midland, MI (US)

( * ) Notice: Subject to any disclaimer, the term of this patent is extended or adjusted under 35 U.S.C. 154(b) by 427 days.

(21) Appl. No.: 12/613,144

(22) Filed: Nov. 5, 2009

(65) Prior Publication Data

US 2010/0121113 A1    May 13, 2010

Related U.S. Application Data

(60) Provisional application No. 61/112,897, filed on Nov. 10, 2008.

(51) Int. Cl.
*C07C 31/20* (2006.01)
(52) U.S. Cl. ........................................ 568/852
(58) Field of Classification Search .................. 568/852
See application file for complete search history.

(56) References Cited

U.S. PATENT DOCUMENTS

| | | | |
|---|---|---|---|
| 4,349,417 | A | 9/1982 | Rebsdat et al. |
| 4,647,705 | A | 3/1987 | Schmitt et al. |
| 4,830,712 | A | 5/1989 | Crandall et al. |
| 5,770,777 | A | 6/1998 | Albright et al. |
| 6,187,973 | B1 | 2/2001 | Husain |
| 6,242,655 | B1 | 6/2001 | Husain |
| 6,395,864 | B1 | 5/2002 | Kuhling et al. |
| 6,437,199 | B1 | 8/2002 | Oka et al. |
| 6,514,388 | B1 | 2/2003 | Adrian et al. |
| 6,605,192 | B1 | 8/2003 | Theis et al. |

FOREIGN PATENT DOCUMENTS

| | | |
|---|---|---|
| CA | 1246617 A1 | 12/1988 |
| DE | 19757707 A1 | 6/1999 |
| GB | 2053190 A | 2/1981 |
| WO | 99/58483 | 11/1999 |
| WO | 2008085268 A1 | 7/2008 |

OTHER PUBLICATIONS

English Language Abstract of DE 197 57 707, Jun. 24, 1999.
International Search Report and Written Opinion of related application PCT/US2009/063070, Jun. 10, 2010.

*Primary Examiner* — Sikarl Witherspoon
(74) *Attorney, Agent, or Firm* — Lois K. Ruszala; KSJLaw, LLC

(57) ABSTRACT

The present invention provides a process for producing low color glycols that comprises altering at least one condition of a reaction component and/or process stream within the process to be unfavorable for the formation of at least one color-producing contaminant intermediate. As such, such intermediates may be reduced in concentration, or even eliminated entirely, from glycols produced by the process. Since they are not present, or are present in reduced number, the intermediates cannot form color-producing contaminants in the glycols, and low color glycols are provided to the customer. Any condition that can discourage the formation of color forming contaminant intermediates can be adjusted, although conditions that can be adjusted by materials or equipment already utilized in the process, e.g., temperature, pressure, pH, concentration of a color-forming contaminant precursor, the presence of one or more solvents or catalysts favorable for the production of the color-producing contaminant or contaminant intermediate, and the like, are preferred.

12 Claims, 1 Drawing Sheet

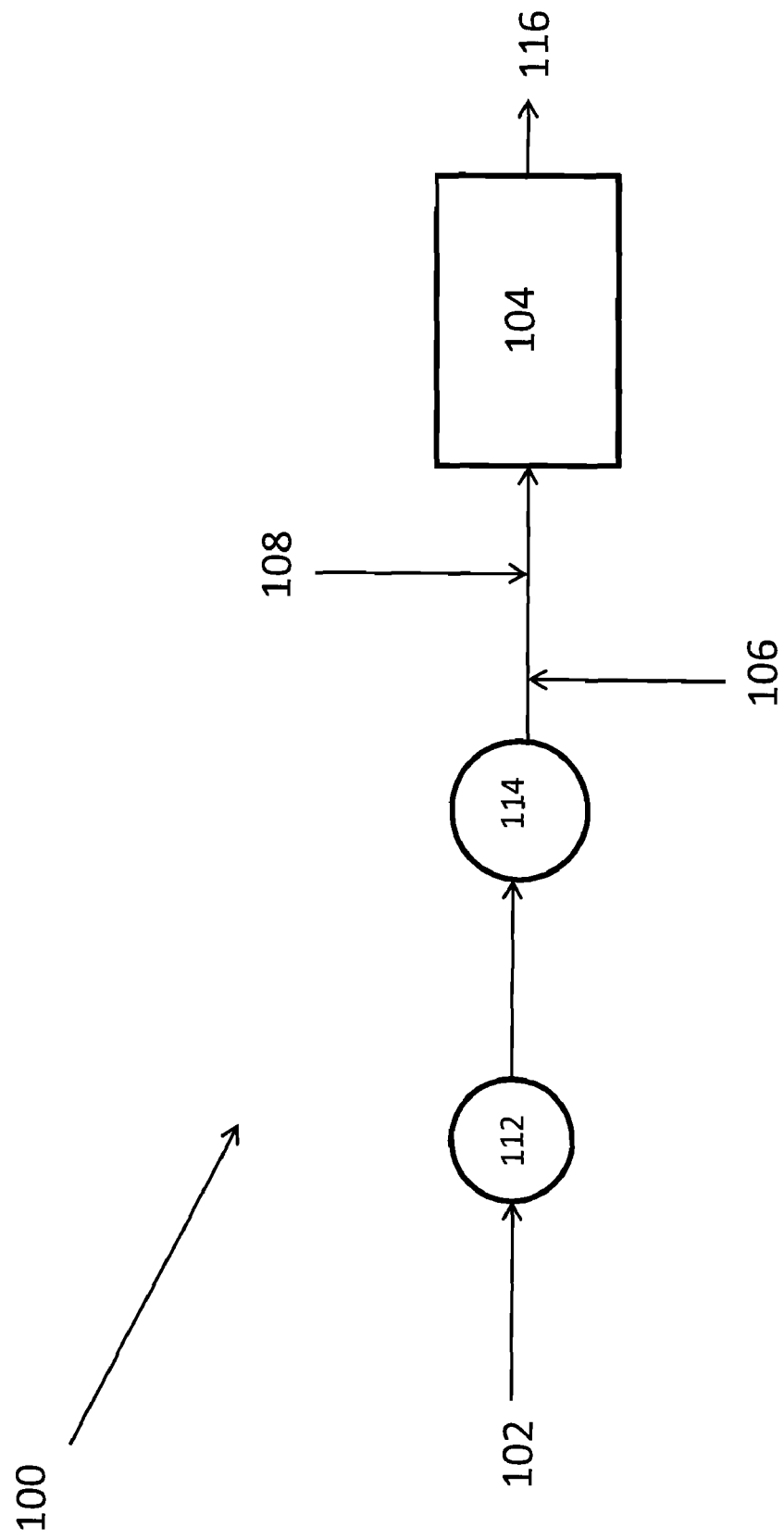

PROCESS FOR PRODUCING LOW COLOR GLYCOLS

FIELD

The present invention provides a process for producing low color glycols. More specifically, the process of the present invention involves altering at least one condition of a reaction component and/or process stream, e.g., temperature, pressure, pH, the concentration of at least one color producing contaminant precursor, etc., within the process to be unfavorable for the formation of at least one color-producing contaminant intermediate.

BACKGROUND

Even though not necessarily readily perceivable by consumers, commodity chemicals are ubiquitous in commercial channels. Many end-products incorporating commodity chemicals have specific cosmetic properties that are desired or required for consumer acceptance, and thus, commercial success. For example, many commodity chemicals, such as ethylene glycols or other glycols, are utilized in the production of fibers or foams that are subsequently utilized in the production of fabric or cushions later incorporated into articles introduced into the garment, transportation, sporting goods, household goods, etc. streams of commerce. Commercial acceptance and/or success of several, if not all, of these, may at least partially depend upon the ability to produce these articles in a specific color or color pattern.

In order to provide these chemicals with the initial color and/or dye integrity required by some customers, the chemicals typically must be of high purity, i.e., they are desirably substantially free of quantities of impurities that may impact the reproducible dyeability of the end product and/or impurities that absorb light in the visible region of the spectrum. As such, much effort has been focused on developing processes or methods for providing higher purity chemicals intended for use in such applications. Passing the chemicals through various filtration systems, e.g., comprising charcoal and/or ion exchange resins, can in some cases result in an improvement of the purity of the chemical, however, this method adds time and expense to the manufacturing process. Distillation has also been employed, and can result in separated fractions suitable for use in both high and low purity applications. Similar to filtration, however, distillation can add undesirable time and expense to the manufacturing process. Further, in some cases, distillation and filtration may not remove all, or enough of, the impurities to provide high purity chemicals.

Finally, some have attempted to control the formation of ultra-violet absorbing contaminants in such chemicals by adjusting the pH of the process used to produce them through acid addition. However, the addition of acids into many manufacturing processes can be problematic not only for the additional cost of the acid itself, but also because it can lower the pH to such an extent that damage can occur to processing equipment downstream from the acid addition. Further, efforts to control pH late in the manufacturing process may be thwarted by the presence of reaction products and by-products that influence the pH reading. In fact, if the pH is measured too late in the process, the offending by-products may have already been formed rendering any adjustments made to the pH superfluous. No methods known to Applicants have been provided that attempt to reduce the presence or formation of contaminants that absorb light in the visible portion of the spectrum, even though such contaminants can be, and often times are, just as objectionable, if not more objectionable, to the customers of such chemicals as UV absorbing contaminants.

Desirably, a process would be provided for producing low color glycols. The advantage of such a process would be amplified if it did not require the use of additional steps or equipment, and could be even further leveraged if it made use of reactants already utilized in the manufacturing process. Any such process would also desirably not include components capable of corroding or otherwise causing damage to existing equipment or creating additional safety issues.

SUMMARY

The present invention provides a process for producing low color glycols. More specifically, the process of the present invention involves altering at least one condition of a reaction component and/or process stream within the process to be unfavorable for the formation of at least one color-producing contaminant intermediate. As such, such intermediates may be reduced in concentration, or even eliminated entirely, from glycols produced by the process. Since they are not present, or are present in reduced number, the intermediates cannot form color-producing contaminants in the glycols, and low color glycols are provided to the customer. Preventing or reducing the formation of color producing intermediates can be a superior method of providing low color glycols as compared to methods attempting to inhibit the conversion of the intermediates to the color producing contaminants since, in many instances, once the color producing intermediates are produced, their conversion to the color producing contaminants is inevitable and/or may be caused by conditions of shipping and/or storage out of the manufacturer's control.

In a first aspect then, the present invention provides a process for producing low color glycols. More particularly, the process comprises altering at least one condition of at least one of a reaction component and/or process stream within the process to be unfavorable for the formation of at least one color-producing contaminant intermediate. Although any condition that may affect the formation of the color-producing contaminant intermediate may be altered so as to discourage said formation, those that can conveniently be altered via mechanisms or components already utilized in the particular process are preferred. These are expected to include temperature, pressure, pH, the concentration of at least one color-producing contaminant precursor, the presence of one or more solvents or catalysts favorable for the production of the color-producing contaminant or contaminant intermediate, combinations of these, and the like.

It is also contemplated that multiple reaction components and/or process streams may advantageously have multiple conditions altered, i.e., and so more than one reaction component and/or more than one process stream may have the temperature, pressure and/or pH associated therewith altered and/or may also have the concentration of at least one color-producing contaminant precursor minimized. Low color glycols produced by the present inventive process will advantageously have color averages of less than about 5.0 platinum cobalt units (PCU), less than about 4.0 PCU, or even less than about 3.0 PCU.

DESCRIPTION OF THE DRAWINGS

The detailed description of the invention that follows may be further understood and/or illustrated when considered along with the attached drawings. In order to simplify the drawings, conventional details, such as valves, pumps, condensers, reboilers, surge tanks, flow and temperature control devices and others like these may have been omitted in certain instances. The construction, operation and function of such devices, as well as the appropriate use thereof in process design, is believed to be known to those of ordinary skill in the chemical engineering art and as such, the omission or inclusion of these conventional elements is not meant to impart any particular importance thereto.

FIG. 1 is a schematic diagram of one embodiment of a glycol reaction apparatus according to the present invention.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to bely any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). Unless otherwise defined, all percents are provided as weight percents.

The present invention provides an improved process for the manufacture of low color glycols. It has now been surprisingly discovered that, by altering at least one condition within a reaction component and/or of a process stream so that the formation of at least one color producing contaminant intermediate is discouraged, glycols can be produced that are of sufficient purity to be suitable for use in applications requiring low color glycols. As used herein, the phrase 'low color' is meant to indicate glycols with a color average of less than about 5.0 platinum cobalt units (PCUs). The improved process can be capable of producing glycols with a color average of less than about 5 PCU, or less than about 4.0 PCU, or even less than about 3.0 PCU. Color average as used herein can be measured by ASTM D1209-05.

The fact that the process of the present invention is effective to at least reduce, if not eliminate, color-producing intermediates from the glycols produced by the process is an important advantage of the present invention, since oftentimes, the reactions that occur to convert the color-producing intermediates to the color-producing contaminants may be unavoidable under normal commercial storage, shipping and/or handling conditions. That is, conditions in many commercial channels can be conducive to the occurrence of dehydration and/or oxidation reactions, which in turn, can produce molecules having a conjugated system of bonds of sufficient length to absorb light in the visible spectrum. Rather than relying on the prevention of such conditions, the process of the present invention provides low color glycols by minimizing, the concentration of the color-producing contaminant intermediates, or even eliminating them entirely.

While many chemicals are expected to potentially benefit from the principles of the present invention, those that are susceptible, because of their chemistry, the chemistry of their starting materials or nature of the manufacturing processes or reactions utilized to produce them, to the formation of color producing contaminant precursors, intermediates or contaminants, are preferred candidates for application of the present inventive process. Many of these may desirably be used in applications requiring colorlessness, a particular color, and/or the dye integrity required to reproducibly achieve the desired or required color, and any of these may be particularly preferred. Particular examples of uses in which a high degree of dye integrity and/or initial colorlessness is often required in order to be commercially acceptable include any of the applications in which fibers and foams are utilized. One particular example of a class of chemicals that finds use in fiber and foam applications are the glycols, including, but not limited to, ethylene glycols.

As used herein, the term 'color-producing' is meant to indicate chemical entities that reflect light from at least a portion of the visible spectrum. A 'precursor' is meant to indicate a chemical entity that can react to form an 'intermediate', and an 'intermediate' is a chemical entity that can react to form a color-producing 'contaminant'. While for the sake of consistency the precursors and intermediates referred to herein are referred to as 'color-producing' it is to be understood that neither the precursors nor intermediate must reflect visible light, but rather are capable of reacting to produce the contaminant capable of reflecting visible light, i.e., to produce color. Further, reference to a precursor is not meant to indicate that in each process in which the principles of the present invention are expected to find utility, that a precursor must be formed, or otherwise be present, at all. All that is required is that the process be one that is susceptible to the formation, of a chemical entity that can lead to the formation of a color-producing contaminant.

It has now been surprisingly discovered that the prevention, or at least minimization, of the formation of color-producing contaminant intermediates can provide a more effective means of providing low color glycols as compared to processes which rely solely on the removal of the color-producing contaminant intermediates or contaminants themselves. Firstly, methods of removal of such contaminants or their intermediates are typically time consuming and costly, both of which tend to increase depending on the level of removal required. That is, it may be impossible to remove 100% of one or more of color-producing contaminant intermediates and/or contaminants themselves without incurring prohibitive cost, if it is possible to do so at all. Secondly, in many instances, the conversion of a color producing contaminant intermediate to the contaminant itself may be unavoidable. For example, in many instances the color-producing contaminant intermediates may be polyunsaturates that readily and easily undergo oxidation and/or dehydration to produce contaminants capable of reflecting visible light, and thus producing color.

The process of the present invention applies this discovery and rather than relying on such removal methods alone, alters one or more conditions of at least one reaction component or process stream within the process so that the formation of such color-producing contaminant intermediates is discouraged. As used herein, the phrase 'within the process' is not meant to indicate or require a particular physical relationship to the process, but rather is meant only to indicate that a reaction component or process stream is part of the overall process utilized to place the chemical into the state in which it will be provided to the customer. As such, the reaction component or process stream can be one associated with the formation, purification or separation/fractionation of the chemical, or with any other process utilized in the production of the chemical in the state in which it is provided to the customer. Further, the phrase 'reaction component' is meant to indicate any component associated with the process, and as such, can include reactors, distillation columns, flash drums, heat exchangers, tanks, etc.

Any condition capable of impacting the presence or formation of a color-producing contaminant intermediate can be altered so as to discourage the same. Examples of these include, but are not limited to, the presence of precursors capable of forming the color-producing contaminant intermediate, and conditions that may impact the formation of the color-producing contaminant precursor and/or intermediate. Typically such conditions may include pH, temperature, pressure, the presence of water, any other solvents, and/or the presence of any materials capable of acting as catalysts for the reaction, and the like.

In certain embodiments of the invention, the condition altered may desirably be one readily and easily altered via mechanisms already utilized and available to the process. Many processes for the production of glycols already incorporate mechanisms for altering the temperature or pressure of reaction components and/or process streams within the process, and in processes where the pH is a factor in the formation of the desired chemical, mechanisms for altering or maintaining the same are typically in place. Also, in many instances, higher grades of the reactants and/or solvents used in the process are available and may be utilized, and if not readily available, lower grade solvents or reactants may be subjected to purification steps prior to introduction into the process.

As but one example of the application of the principles of the present invention, one or more conditions that may be altered in connection with the production of, e.g., ethylene glycols, include pH and the concentration of at least one color-producing contaminant precursor. More particularly, ethylene oxide may typically contain at least residual amounts of acetaldehyde. Reducing the amount of acetaldehyde within the ethylene oxide, as may be done by purchasing a higher grade or purity, or by subjecting the ethylene oxide feed to conditions suitable to remove at least a portion of the acetaldehyde, would be one example of a condition of a process stream being altered to discourage the formation of a color producing contaminant intermediate. Further, ensuring that the pH stays below 10 so that the aldol condensation reactions are slowed or do not take place, but above 7 so that the glycol reaction yields a higher amount of monoethylene glycol relative to higher glycols is another example of altering a condition of a reaction component or process stream to discourage the formation of a color-producing contaminant intermediate.

More particularly, in those embodiments of the invention wherein the process is desirably used to produce low color ethylene glycols, the process may comprise altering the purity of the incoming ethylene oxide, and/or the pH within the reaction component and/or of the process stream prior to entry into the reaction component. Depending on purity and/or grade, ethylene oxide may typically contain trace amounts of aldehydes or acetaldehydes as contaminants. While the amounts may be perfectly acceptable for use in processes where low color product are not desired or required, aldehydes and acetaldehydes are considered to be color-producing precursors in that they can participate in conjugation reactions to produce color producing intermediates (conjugated acetaldehydes) that, in turn can readily react to form color producing contaminants. The reduction of any concentration of aldehydes or acetaldehydes that may otherwise be present in the ethylene oxide is thus considered to be a condition of a process stream that may advantageously be altered according to the process of the present invention.

Additionally, and while the reaction of ethylene oxide and water to provide glycols generally will proceed at a commercially acceptable rate under the conditions, at which the ethylene oxide is supplied to the ethylene glycol plant, the reaction may not provide the relatively higher yield of monoethylene glycol as compared to higher glycols that is typically desired in such reactions. The pH may thus typically be adjusted, i.e., to a pH of at least about 7, to ensure preferential production of monoethylene glycol. However, it has now been discovered that if the pH is adjusted beyond a certain degree, further enhancement in the proportion of monoethylene glycol relative to higher glycols may not necessarily be seen, and further, any color producing contaminant precursors or intermediates present may be encouraged to undergo the reactions necessary to form color producing contaminants. That is, at a pH of about 10 or greater, at least a portion of any acetaldehyde present in the ethylene oxide may combine via aldol condensation reactions to form polyunsaturates that in turn, will reflect light in the visible portion of the spectrum. Applying the principles of the present invention, and in addition to e.g., reducing the concentration of acetaldehyde in the ethylene oxide, the pH within the glycol reactor may also be altered to be such that the ethylene oxide/water reaction to monoethylene glycol will proceed at a commercially acceptable rate, but yet so that the aldol condensation reactions will be discouraged, i.e., the pH may desirable be altered to be from about 7 to about 10. Ethylene glycols produced by this embodiment of the present invention are expected to comprise a lower concentration of color-producing contaminant intermediates, and thus, a lower concentration of color producing contaminants that may be formed from them.

The condition desirably altered to discourage the formation of the color-producing contaminant intermediate may be altered by any known method. Preferably, the condition is desirably altered by a mechanism already utilized in connection with the process, so that cost and time savings are provided. However, there are many methods for adjusting, e.g., temperature, pressure, pH, and the concentration of color-producing precursors, that are commercially available at a reasonable cost, and any of these may be added to the process if need be. Further, the condition may be altered directly or indirectly, that is, either by acting directly on the reaction component or process stream, or indirectly, by acting on a component or reactant operatively disposed so that action on the reaction component or reactant is transferred to the reaction component and/or process stream. For example, the temperature within a reaction component within the process can be adjusted by the application of heat, by radiant, convective or conductive means, to the reaction component itself, or to one or more of the reactants being fed into the reaction component. Pressure may typically be adjusted within a process by pumping a fluid out of, or into, the process.

pH may typically be adjusted directly, i.e., by the addition of a material having the desired pH to the process stream, or indirectly, i.e., by adjusting the pH of a feed stream via the addition of such a material. In those embodiments of the invention wherein pH is desirably the condition that is altered, it is to be understood that any related measurement, or measurement convertible to pH, may be utilized, and the appropriate conversion made in order to effectuate the present invention and realize the benefits thereof. For example, if hydrogen ion activity is more easily measured, the pH may be calculated by the following equation: $pH = -\log_{10} \alpha_{H+}$. Furthermore, pH may be measured by any suitable method or with any suitable piece of equipment, as long as whatever the method or equipment used it is calibrated prior to measurements being taken according to the manufacturer's protocol. Typically, pH is desirably and conveniently measured by any of the many commercially available pH meters.

If the pH is desirably altered from an acidic or neutral state to a more basic state, materials having a pH of greater than 7 may desirably be added. Materials having a pH of greater than 7 include any material capable of contributing hydroxide ions to the reaction component or process stream, e.g., caustics or alkalis, one or more alkali metals, one or more alkaline earth metals, one or more concentrated or anhydrous weak bases, or combinations of these. Of these, those capable of being added as liquids are preferred, and caustics and alkalis based upon Group 1 metals on the periodic table are particularly preferred. Examples of these include sodium hydroxide, potassium hydroxide, lithium hydroxide, etc. Because of its ready availability, sodium hydroxide is one example of a particularly preferred caustic. If the pH is desirably altered from a basic or neutral state to a more acidic state, materials having a pH of less than 7 may desirably be added. Materials having a pH of less than about 7 include any material capable of contributing hydrogen ions to the reaction component or process stream. Common acids include mineral acids, sulfonic acids and carboxylic acids, and any of these, others known to those of ordinary skill in the art and combinations of these. In many processes, it may be particularly advantageous for the pH adjustment to be carried out with basic materials, rather than acidic materials, so that any equipment damage or safety issues that may be associated with the same can be avoided.

If desired, multiple pH adjustments may be carried out within the process. For example, pH may be measured and adjusted downstream from the glycol reactor, before or after any equipment in place to remove water from the glycols product stream or before or after any fractionation or separation equipment downstream thereof. Although such measurements may be influenced by the presence of reaction products or any color-producing contaminant precursors or intermediates already formed, such embodiments may nonetheless be capable of providing further reductions in the concentration of color-producing contaminant precursors, intermediates and/or contaminants themselves and are considered to be within the scope of the present invention, especially when utilized in conjunction with a pH measurement and adjustment prior to entry of a process stream into, or within, a glycol reactor.

Appropriate ranges for the condition altered will depend on the particular glycol being produced by the process and the color-forming contaminant intermediate whose formation is desirably discouraged. Desirably, the condition altered will be capable of being adjusted to discourage the formation of the color-producing contaminant intermediate while not interfering substantially with, if at all, the production of the glycol. The condition will further desirably be capable of being altered to discourage the formation of the color-producing contaminant intermediate within safe boundaries, as well as boundaries that are not substantially detrimental to the other pieces of equipment utilized in connection with the process. The condition would desirably also not be altered beyond the extent that has an impact on the formation of the color-producing contaminant intermediate, if only in the interest of practicality.

Turning to FIG. 1, there is illustrated a portion of an apparatus 100 according to the present invention. Apparatus 100 generally comprises reactant feed 102, reactor 104, pH adjusting feed 106 and pH measurement apparatus 108.

In operation, a process stream of a mixture of reactants is fed into the apparatus and passed through heat exchanger 112, which may optionally be used to preheat the process stream and feed pump 114 to increase the pressure of the process stream and. Property adjusting material may be added via addition line 106, and a property of the process stream then measured by property measurement apparatus 108. These measurements may be static or relatively continuous, and if static, any number may be taken at any time interval. The measurement(s) taken by property measuring apparatus 108 may be used to adjust the output of property adjusting addition line 106, if desired or required. The process stream is fed into reactor 104. The resulting product family is discharged from reactor 104 and provided to further processing equipment downstream (not shown) for, e.g., the removal of water and/or fractionation of reaction products.

FIG. 1 can be used to further describe those particular embodiments of the invention wherein ethylene oxide is desirably reacted with water to produce low color ethylene glycols. In these embodiments, feed 102 would be used to introduce ethylene oxide and water into reactor 104, a glycol reactor in these embodiments of the invention. As those of ordinary skill in the art are aware, the glycol stream produced by apparatus 100 would typically be subjected to downstream processes for the removal of water, and/or separation/fractionation of glycols. These downstream processes are not shown in FIG. 1, and will not be discussed further herein. For a description of glycols generally, including the manufacture thereof, as may include such water removal and separation/fractionation equipment, reference may be made to "Glycols", M. W. Forkner et al, Kirk-Othmer Encyclopedia of Chemical Technology, 2004, the entirety of which hereby being incorporated herein by reference for any and all purposes.

For the production of ethylene glycols, a mixture of ethylene oxide and water is fed into apparatus 100 and may typically comprise from about 6 wt % to about 14 wt % ethylene oxide with the remainder water, or stated another way, may comprise ratios of from about 6:1 to about 14:1 of water to ethylene oxide. The ethylene oxide (EO) and water may be heated to temperatures of from about 100° C. to about 120° C. prior to introduction into apparatus 100, or they may be introduced at ambient temperature, or at substantially the desired reaction temperature, if desired. In many conventional processes, the EO/water process stream is fed through heat exchanger 112 to raise the temperature of the EO/water process stream to at least about 130° C. and desirably, from about 155° C. to about 175° C., and then feed pump 114 to increase the pressure thereof to at least about 20 bars. In many conventional processes, the pH of the reactants necessitates the addition of a pH lowering material, and so, if desired or required, caustic may be added to the process stream by property adjusting material line 106. The pH of the EO/water process stream is then desirably measured with property measuring apparatus 108, which in this embodiment would be a pH meter, and, if necessary, adjusted to be basic, but yet less than about 10. As mentioned hereinabove, any material capable of effecting such an adjustment may be utilized. Since sodium hydroxide is readily available and cost effective, it typically may be utilized for this purpose. Further, any concentration of the desired material may be utilized to adjust the pH although it would be expected that more sensitive adjustments may be possible with lower concentrations of material. In those embodiments where sodium hydroxide is desirably used to adjust the pH to greater than about 7, but yet less than about 10, concentrations of about 20 wt % may be conveniently obtained and utilized.

The process stream exiting glycol reactor 104 is expected to comprise from about 10 to about 20 weight % (wt %) mixed glycols, from about 90 to about 80 wt % water and less than about 10 ppm unreacted EO. In order to prevent vaporization of any such residual amounts of EO, the pressure on outlet line 116 is desirably maintained at greater than about 21.6 bars. The process stream, which may typically comprise about 60 wt % mixed glycols which further comprise from about 90 wt % to about 95 wt % monoethylene glycol, is fed from line 116 to downstream processing equipment for further processing.

The following example is set forth for the purpose of illustrating the invention; but this example is not intended to limit the invention in any manner. One skilled in the art will recognize a variety of substitutions and modifications of the example that will fall within the scope of the invention.

EXAMPLE 1

An apparatus similar to that shown in FIG. 1, for the reaction of ethylene oxide and water to produce ethylene glycols, will be modified so that product (mono ethylene glycol) coming off a side stream will go up in color at least 2.0 units, while on spec product will yet also be produced into main product tanks (not shown in FIG. 1). Such an apparatus will typically produce refined product about 6 hours after leaving the glycol reactor, and it is this refined product that will be subject to color testing. No samples will be collected until the apparatus had been operating at steady state for at least 24 hours, and once at steady state for at least this period of time, samples will be collected and analyzed for color at least once per hour.

pH measuring apparatus 122, an ABB AX460 pH meter, will be calibrated prior to initiation of the test, and the pH of the process stream prior to entry into the reactor confirmed to be about 8.5+/−0.3. During the test period, the percent open of the caustic (20% sodium hydroxide) metering pump stroke, and thus the pH, will be the only variables. All other operating parameters, i.e., temperature of feeds, temperature of process stream, temperature and pressure within lines and reactors, will remain substantially constant.

For the initial test period, the caustic metering pump stroke will be increased slowly, over a period of several hours to ensure that on spec product will still be produced into the main tanks. The hourly metering pump stroke value, and the resulting pH reading and color averages are provided in the below table. Each hourly sample was taken in triplicate and the pH readings and color averages provided are the average of the three readings.

TABLE 1

| Time | Caustic inlet, % open | pH reactor inlet | Color average |
| --- | --- | --- | --- |
| $T_0$ | 17 | 8.56 | 2.4 |
| $T_0 + 1$ | 17 | 8.55 | 2.4 |
| $T_0 + 2$ | 20 | 8.51 | 2.4 |
| $T_0 + 3$ | 30 | 8.56 | 2.4 |
| $T_0 + 4$ | 35 | 8.69 | 2.5 |
| $T_0 + 5$ | 70 | 8.91 | 2.3 |
| $T_0 + 6$ | 70 | 9.05 | 2.2 |
| $T_0 + 7$ | 80 | 9.11 | 2.2 |
| $T_0 + 8$ | 100 | 9.21 | 2.1 |
| $T_0 + 9$ | 100 | 9.24 | 2.6 |
| $T_0 + 10$ | 100 | 9.25 | 4.4 |
| $T_0 + 11$ | 17 | 8.99 | 6.8 |
| $T_0 + 12$ | 17 | 8.74 | 6.9 |
| $T_0 + 13$ | 17 | 8.54 | 7.0 |
| $T_0 + 14$ | 17 | 8.51 | 4.5 |
| $T_0 + 15$ | 17 | 8.49 | 4.8 |
| $T_0 + 16$ | 17 | 8.48 | 4.3 |
| $T_0 + 17$ | 17 | 8.49 | 3.9 |
| $T_0 + 18$ | 17 | 8.48 | 3.1 |
| $T_0 + 19$ | 17 | 8.48 | 2.9 |
| $T_0 + 20$ | 100 | 8.64 | 3.0 |
| $T_0 + 21$ | 100 | 9.26 | 3.1 |
| $T_0 + 22$ | 100 | 9.28 | 3.1 |
| $T_0 + 23$ | 100 | 9.26 | 5.0 |
| $T_0 + 24$ | 100 | 9.25 | 5.9 |
| $T_0 + 25$ | 100 | 9.24 | 7.4 |
| $T_0 + 26$ | 17 | 8.89 | 7.4 |
| $T_0 + 27$ | 17 | 8.51 | 7.3 |
| $T_0 + 28$ | 17 | 8.44 | 6.2 |
| $T_0 + 29$ | 17 | 8.41 | 5.5 |
| $T_0 + 30$ | 17 | 8.39 | 4.0 |
| $T_0 + 31$ | 17 | 8.36 | 2.4 |
| $T_0 + 32$ | 20 | 8.44 | 2.3 |
| $T_0 + 33$ | 18 | 8.53 | 2.2 |
| $T_0 + 34$ | 17 | 8.52 | 2.1 |
| $T_0 + 35$ | 16 | 8.48 | 2 |

As shown by the results above, product collected about 6-7 hours after the caustic metering pump stroke is increased to greater percentages open show an increase in color average as compared to product taken that is representative of the caustic metering pump stroke being at the normal level, i.e., 17%. The increase in caustic metering pump stroke open percent results in pH values as high as 9.28, and color average of product collected 6-7 hours later (subject to the process stream condition of pH as high as 9.28) is as high as about 7.4. Color averages of over about 5 are not considered commercially acceptable for many applications.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. A process for producing a low color glycol comprising altering at least two conditions of at least one of a reaction component and/or process stream within the process to be unfavorable for the formation of at least one color-producing contaminant, wherein the at least two conditions comprise altering the pH to be between about 7.0 and 10 and reducing the concentration of at least one color-producing contaminant precursor and wherein the low color glycol has a color average of less than about 5.0 platinum cobalt units.

2. The process of claim 1, wherein the at least two conditions further comprise temperature, pressure, the presence of one or more solvents or catalysts favorable for the production of the color-producing contaminant or contaminant intermediate or combinations of these.

3. The process of claim 1, wherein at least two of a reaction component and/or process stream have at least two conditions altered.

4. The process of claim 1, wherein the low color glycol has a color average of less than about 4.0 color average platinum cobalt units.

5. The process of claim 4, wherein the low color glycol has a color average of less than about 3.0 color average platinum cobalt units.

6. The process of claim 1, wherein the glycol comprises an ethylene glycol.

7. The process of claim 6, wherein the glycol comprises monoethylene glycol.

8. The process of claim 6, wherein the at least two conditions further comprise temperature, pressure, the presence of one or more solvents or catalysts favorable for the production of the color-producing contaminant or contaminant intermediate, or combinations of these.

9. The process of claim 1, wherein the at least one color-producing contaminant precursor comprises acetaldehyde.

10. The process of claim 9, wherein the pH is altered to be greater than about 7.0 and less than about 9.5.

11. The process of claim 10, wherein the pH is altered to be greater than about 7.0 and less than about 9.0.

12. The process of claim 1, wherein a glycol reactor has the pH therein altered and a process stream has the concentration of at least one color-producing contaminant precursor therein altered.

* * * * *